United States Patent [19]
Ringle et al.

[11] Patent Number: 5,311,889
[45] Date of Patent: May 17, 1994

[54] DENTAL FLOSS & PRE-THREADED LEADER

[75] Inventors: Larry L. Ringle, Sacramento; Ronald G. Lax, Grass Valley, both of Calif.

[73] Assignee: CSM Patents, Inc., Sacramento, Calif.

[21] Appl. No.: 12,658

[22] Filed: Feb. 1, 1993

Related U.S. Application Data

[63] Continuation-in-part of Ser. No. 712,405, Jun. 10, 1991, Pat. No. 5,183,063.

[51] Int. Cl.$^5$ .............................................. A61C 15/00
[52] U.S. Cl. ..................................... 132/321; 132/329
[58] Field of Search ............... 132/321, 323, 327, 329; 433/2, 3; 223/99, 102

[56] References Cited

U.S. PATENT DOCUMENTS

| | | | |
|---|---|---|---|
| 119,745 | 10/1871 | Cowardin . | |
| 1,801,691 | 4/1931 | Ripper | 223/102 |
| 2,381,142 | 8/1945 | Stonehill | 18/59 |
| 2,612,177 | 9/1952 | Footer | 132/93 |
| 2,620,104 | 12/1952 | Graham | 223/102 |
| 2,721,014 | 10/1955 | Allen | 223/102 |
| 2,931,371 | 4/1960 | Petitta | 132/89 |
| 3,160,157 | 12/1964 | Chisman | 128/339 |
| 3,525,460 | 8/1970 | Hendy | 223/102 |
| 3,531,030 | 9/1970 | Doiron | 223/102 |
| 3,650,392 | 3/1972 | Haagedoorn | 206/56 AC |
| 3,744,499 | 7/1973 | Wells | 132/92 A |
| 3,837,351 | 9/1974 | Thornton | 132/89 |
| 3,838,702 | 10/1974 | Standish et al. | 132/89 |
| 3,880,167 | 4/1975 | Hardwick | 128/339 |
| 3,896,824 | 7/1975 | Thornton | 132/89 |
| 3,910,282 | 10/1975 | Messer et al. | 128/339 |
| 3,929,144 | 12/1975 | Tarrson et al. | 132/323 |
| 3,930,059 | 12/1975 | Wells | 427/2 |
| 3,949,756 | 4/1976 | Ace | 128/339 |
| 3,987,839 | 10/1976 | Pace | 163/5 |
| 4,008,727 | 2/1977 | Thornton | 132/321 |
| 4,008,836 | 2/1977 | Herzstein | 223/99 |
| 4,011,658 | 3/1977 | Tarrson et al. | 32/40 R |
| 4,029,113 | 6/1977 | Guyton | 132/91 |
| 4,064,883 | 12/1977 | Oldham | 132/93 |
| 4,070,815 | 1/1978 | Negishi et al. | 57/140 J |
| 4,080,777 | 3/1978 | Griset, Jr. | 57/140 |
| 4,133,339 | 1/1979 | Naslund | 132/89 |
| 4,142,538 | 3/1979 | Thornton | 132/321 |
| 4,155,216 | 5/1979 | Griset, Jr. | 57/295 |
| 4,159,619 | 7/1979 | Griset, Jr. | 57/295 |
| 4,182,341 | 1/1980 | Perri | 128/339 |
| 4,184,316 | 1/1980 | Griset, Jr. | 57/295 |
| 4,215,478 | 1/1980 | Thomas et al. | 433/25 |
| 4,265,258 | 5/1981 | Eaton, II | 132/93 |
| 4,274,565 | 6/1981 | Russell | 223/102 |
| 4,277,297 | 7/1981 | Thornton | 156/161 |
| 4,296,877 | 10/1981 | Lubow | 223/99 |
| 4,385,575 | 5/1983 | Weber | 112/224 |
| 4,441,497 | 4/1984 | Paudler | 128/339 |
| 4,512,164 | 4/1985 | Fukuhara | 66/121 |
| 4,523,600 | 6/1985 | Donovan | 132/89 |
| 4,583,564 | 4/1986 | Finkelstein et al. | 132/91 |
| 4,602,636 | 7/1986 | Noiles | 128/335.5 |
| 4,667,860 | 5/1987 | Feuerman | 223/99 |
| 4,790,254 | 12/1988 | Vornholt | 112/222 |
| 4,805,292 | 2/1989 | Noguchi | 29/445 |
| 4,817,398 | 4/1989 | Sos et al. | 66/121 |
| 4,832,063 | 5/1989 | Smole | 132/329 |
| 4,832,240 | 5/1989 | Dalbo | 223/99 |
| 4,901,722 | 2/1990 | Noguchi | 606/223 |
| 5,035,707 | 7/1991 | Korthoff | 606/224 |
| 5,038,836 | 8/1991 | Caramaschi | 139/11 |
| 5,050,625 | 9/1991 | Siekmann | 132/323 |
| 5,089,012 | 2/1992 | Prou | 606/224 |
| 5,129,558 | 7/1992 | Feuerman | 223/102 |
| 5,133,738 | 7/1992 | Korthoff et al. | 606/224 |

Primary Examiner—Gene Mancene
Assistant Examiner—Frank A. LaViola
Attorney, Agent, or Firm—Bernhard Kreten

[57] ABSTRACT

An integrally formed dental floss and leader which lends itself to oral prophylaxis especially for implants and bridges. The floss is captured by the leader through a hinged door which swings from an open to a closed position during fabrication to provide an integral unit for use by a floss user when closed. A leading portion of the door fits flush within a complementally formed support channel within a tethered end of the leader. A trailing portion of the door projects with an extension of a floor of the support channel, defining a tongue, to provide a floss support. A hinge defines a transition between the floor extension and the door. The hinge allows the door to pivot about the floss and enter the support channel with the floss interposed between the door and the tongue. Shoulders border the support channel providing reinforcement to the tethered end.

33 Claims, 2 Drawing Sheets

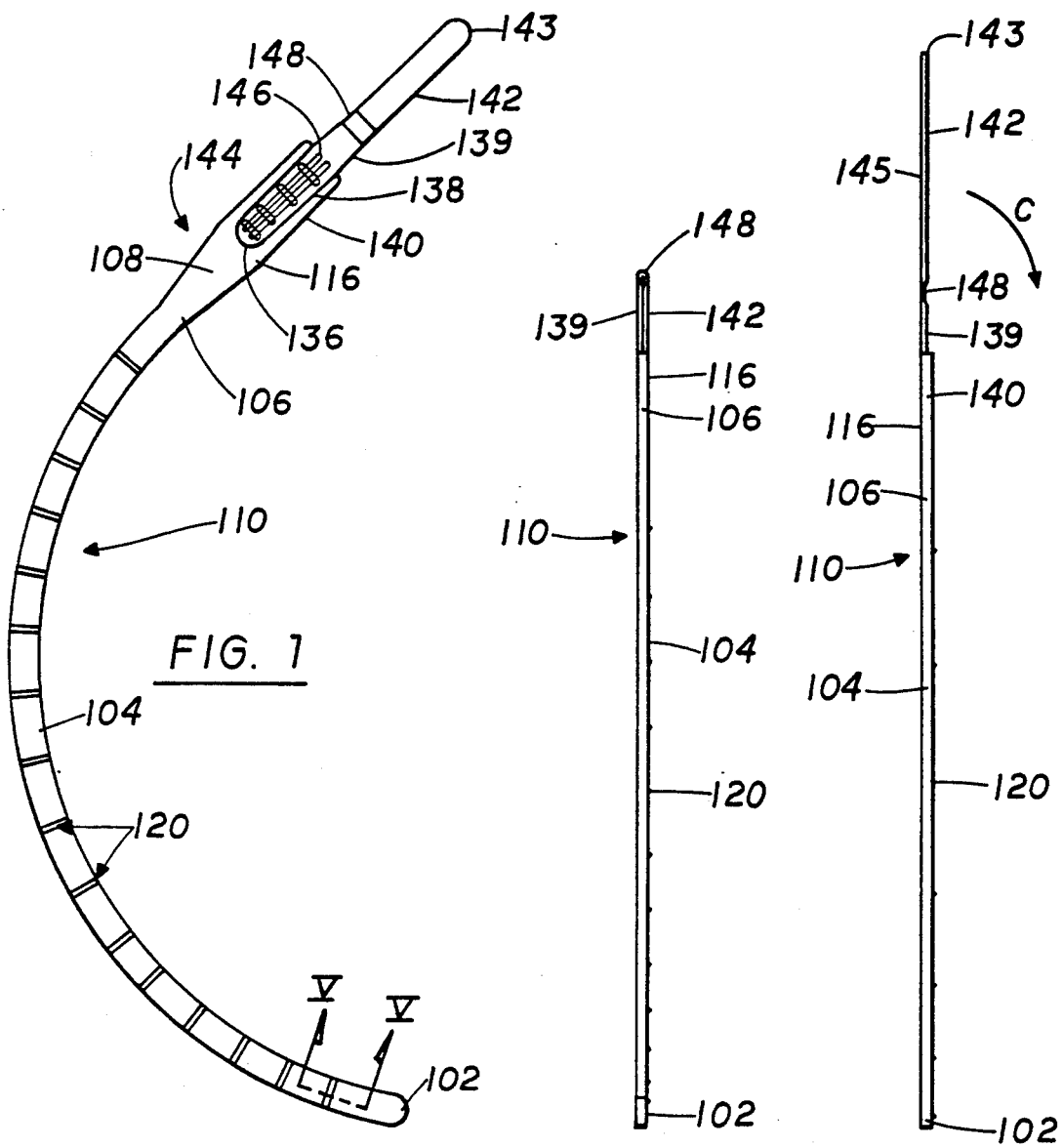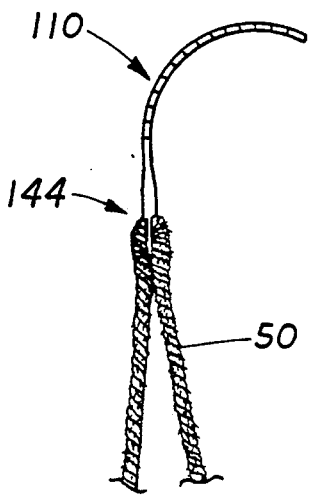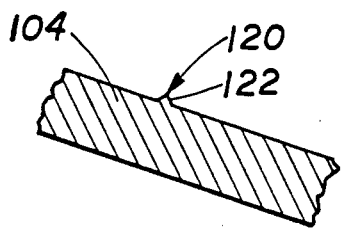

DENTAL FLOSS & PRE-THREADED LEADER

CROSS REFERENCE TO RELATED APPLICATION

This application is a continuation-in-part of application Ser. No. 07/712,405, filed Jun. 10, 1991 now U.S. Pat. No. 5,183,063.

FIELD OF THE INVENTION

The following invention relates generally to an improved form of dental floss having exceptional plaque-removing capabilities and a leader coupled thereto. More particularly, the invention relates to multi-ply acrylic fiber which has an excellent ability to remove plaque and a leader of the type which lends itself for use with dental bridges and implants. A leader is formed on one free end of the acrylic fiber to facilitate placement of the floss in plaque-collecting areas.

BACKGROUND OF THE INVENTION

Since the mid-1960's plaque has been identified as playing at least a major role in causing dental problems both with respect to caries and periodontal disease. However, the actual mechanism by which plaque operates is still subject to conjecture. Plaque, a film of mucus which is produced in the mouth, is a known medium which can harbor bacteria both on the tooth and adjacent gum tissue. It is now generally recognized that removal of plaque is essential for promulgating oral hygiene.

Although substantial research and product engineering has occurred over the last 25 years with a view towards effectively removing plaque, certain difficulties still exist. The following prior art describes the on going efforts of others attempting to solve this long standing problem which has yet evaded solution, and these prior art citations are included to discharge applicant's acknowledged duty to disclose prior art with which he is familiar:

| INVENTOR | PAT. NO. | ISSUE DATE |
| --- | --- | --- |
| Cowardin, C. M. | 119,745 | October 10, 1871 |
| Ripper | 1,801,691 | April 21, 1931 |
| Stonehill | 2,381,142 | August 7, 1945 |
| Footer, J. | 2,612,177 | September 30, 1952 |
| Graham | 2,620,104 | December 2, 1952 |
| Allen | 2,721,014 | October 18, 1955 |
| Petitta, M. | 2,931,371 | April 5, 1960 |
| Chisman | 3,160,157 | December 8, 1964 |
| Hendy | 3,525,460 | August 25, 1970 |
| Doiron | 3,531,030 | September 29, 1970 |
| Haagedoorn | 3,650,392 | March 21, 1972 |
| Wells, R. L. | 3,744,499 | July 10, 1973 |
| Thronton | 3,837,351 | September 14, 1974 |
| Standish et al. | 3,838,702 | October 1, 1974 |
| Hardwick | 3,880,167 | April 29, 1975 |
| Thornton | 3,896,824 | July 29, 1975 |
| Messer, et al. | 3,910,282 | October 7, 1975 |
| Tarrson, et. al. | 3,929,144 | December, 1975 |
| Wells, R. L. | 3,930,059 | December 30, 1975 |
| Ace | 3,949,756 | April 13, 1976 |
| Pace | 3,987,839 | October 26, 1976 |
| Herzstein | 4,008,836 | Februray 22, 1977 |
| Tarrson et al. | 4,011,658 | March 15, 1977 |
| Guyton, W. C. | 4,029,113 | June 14, 1977 |
| Oldham, G. R. | 4,064,883 | December 27, 1977 |
| Negishi, et al | 4,070,815 | January 31, 1978 |
| Griset, Jr. | 4,080,777 | March 28, 1978 |
| Naslund | 4,133,339 | January, 9, 1979 |
| Griset, Jr. | 4,155,216 | May 22, 1979 |
| Griset, Jr. | 4,159,619 | July 3, 1979 |
| Perri, S. | 4,182,341 | January 8, 1980 |
| Griset, Jr. | 4,184,316 | January 22, 1980 |
| Thomas et al | 4,215,478 | August 5, 1980 |
| Eaton, II | 4,265,258 | May 5, 1981 |
| Russell | 4,274,565 | June 23, 1981 |
| Lubow | 4,296,877 | October 27, 1981 |
| Weber | 4,385,575 | May 31, 1983 |
| Paudler | 4,441,497 | April 10, 1984 |
| Fukuhara | 4,512,164 | April 23, 1985 |
| Donovan, M. | 4,523,600 | June 18, 1985 |
| Finkelstein et al | 4,583,564 | April 22, 1986 |
| Noiles | 4,602,636 | July 29, 1986 |
| Feuerman | 4,667,860 | May 26, 1987 |
| Vornholt | 4,790,254 | December 13, 1988 |
| Noguchi | 4,805,292 | February 21, 1989 |
| Sos, et. al. | 4,817,398 | April 4, 1989 |
| Smole, F. T. | 4,832,063 | May 23, 1989 |
| Dalbo | 4,832,240 | May 23, 1989 |
| Noguchi | 4,901,722 | February 20, 1990 |
| Korthoff | 5,035,707 | July 30, 1991 |
| Caramaschi | 5,038,836 | August 13, 1991 |
| Siekmann | 5,050,625 | September 24, 1991 |
| Prou | 5,089,012 | February 18, 1992 |
| Feuerman | 5,129,558 | July 14, 1992 |
| Korthoff, et al. | 5,133,738 | July 28, 1992 |

Generally, the techniques for plaque removal are predicated on two principles. The first involves plaque removal through "washing" the plaque from the mouth area by means of liquids. Second, plaque removal has been attempted by mechanical brushing.

With respect to washing, certain mouthwashes are commercially marketed without prescription which purport to be effective in plaque control. These however are not registered with the Food and Drug Administration, and are listed merely as cosmetics. Available research data suggests that these mouthwashes are less than completely effective. A second known liquid, Peridex, is available under prescription and is a known plaque-removing liquid, but is objectionable to the extent that side effects are exhibited in some individuals. These side effects include adverse teeth staining and affection of one's taste perception. Even with an effective liquid, the film-like quality of plaque thwarts highly efficient removal through mere mouthwashing, and is singularly ineffective when trying to remove plaque in the sulcus area of one's mouth, i.e., the narrow trough-like gap between one's tooth and the gum tissue. This is also critical interproximally (in between the teeth) since this is where most periodontal disease and caries occur. When a patient, already afflicted by periodontal disease or for other reasons, uses dental implants, bridges or has had subgingival curettage or surgery performed, interproximal spaces greater than 4 mm exist between teeth and or adjacent the sulcus. This provides greater opportunity for further plaque formation and gum disease.

To a certain extent, plaque formation is not a problem on tooth surfaces that can receive direct mechanical contact with an instrument such as a brush which effectively breaks up the plaque film and therefore allows the plaque and its associated entrained bacteria to be carried away. Many brush manufacturers claim their bristles will go below the gum (in the sulcus) on the buccal and lingual—but not interproximally. Thus, along those areas where direct brush contact is possible, plaque buildup is less of a problem. However, brushes still are quite ineffective in removing plaque both along the area immediately below the gum line, i.e., the sulcus and interproximally. The problem is exacerbated when patients have had periodontal related dental procedures performed.

As knowledge with respect to the role that plaque plays in dental disease has grown, so too has the change in the design of various types of dental floss. While dental floss was once used substantially as a toothpick for the removal of entrained matter caught between teeth, various changes in dental floss appearance, particularly in the last few years reflect the belief that dental floss can be used to remove plaque in areas normally inaccessible by any other means particularly especially when the floss is used daily. Most designs involve contouring the external configuration of nylon or polyethylene to form an abrasive surface which can break up the plaque film under the gum line and between teeth to solve the problem. Earlier attempts have included the use of fibers formed from silk, cotton, nylon or blends thereof.

All of these known prior art flossing structures are less than desirable in that they are either too abrasive which adversely effects the enamel on the tooth, are too sharp which can cause damage to the gum tissue by cutting the gums, or are ineffective in removing the plaque. Moreover, taking this floss under the gum actually causes pain and the patient, therefore, will not take floss under the gum to remove plaque in the normal 3 mm sulci.

Another problem involves the geometry of prior art leaders themselves. Commercially available threaders for use with bridges, implants, etc. must first be threaded with the floss because they do not come pre-threaded. This can be inconvenient and discouraging to a prospective user. Further the geometry of many threaders make their use further frustrating. Among other things, saliva makes the threader too slippery to use.

Another problem is that extremely small threaders may impose a point load on the floss which makes fracture of the floss likely. When this occurs, the floss is entrained in the person's mouth and can be difficult to remove.

Another problem is that small threaders—typically formed by injection molding—are difficult to make without inducing zones of weakness in the threader. Plastic, such as nylon when unstressed or ideally formed, exhibits long molecular chains for greatest tensile strength. "Hairpin" turns (such as adjacent a threaded eyelet) tend to shorten the molecular chain inducing failure of the threader itself upon tensile loading by the floss.

Other threaders exhibit a "knit-line" caused by the flow of the plastic resin around two sides of a core and re-joining downstream from the core. This knit-line is a natural area of weakness and therefore failure.

SUMMARY OF THE INVENTION

The instant invention is distinguished over the known prior art in that the inventor has discovered that acrylic fiber advantageously removes unwanted plaque yet does so without damaging either the tooth's enamel or gum's tissue. While the exact reasons why acrylic fiber are superior to known prior art materials may be the basis of some speculation and conjecture, the inventor's extensive "split-mouth" studies, comparing the known prior art to acrylic fiber demonstrates efficacy.

One primary reason appears to be the denure or "fuzziness" of the acrylic fiber when it is configured as floss like substance. The acrylic fiber exhibits a plurality of outwardly extending free ends which appear well suited to reach within the bottom most area of the sulcus and gently remove plaque therefrom. It is to be noted that in a healthy mouth, the depth of the trough defining the sulcus is approximately 3 mm interproximally. Plaque is manufactured by the body and forms in this trough area. Since plaque consists of bacteria, "fresh" plaque (i.e., less than 24–36 hours) is not believed to be harmful because it does not contain a high number of pathogenic bacteria. When the plaque becomes old, however, the bacteria present will attack the tooth and tissue area against which it abuts, causing periodontal disease. Regular use of floss formed from acrylic fiber stops the infection.

A second advantage attributable to the use of acrylic fiber as a dental floss involves the coefficient of friction associated with the acrylic fiber when it is configured as a floss like substance. Because the mechanical flossing motion is oscillatory, back and forth along the length of the floss strand, friction is generated and dissipated in the form of heat when using acrylic fiber as a floss. This provides a thermal sensor to the user of the floss as to the relative vigor with which the flossing should be conducted for best results. Unlike prior art fibers used in flossing which have coefficients of friction different from acrylic fiber, and therefore result in either too vigorous or too light a flossing motion, acrylic fiber's coefficient of friction appears to correlate with effective flossing technique.

A third possible reason for the enhanced benefits associated with acrylic fiber according to the instant invention devolves from gingival stimulation and not inflammation as can occur with some prior art devices. The cross-sectional diameter of the floss formed from the acrylic fiber according to the present invention is kept within certain ranges depending upon the characteristics of the flosser's mouth. Factors include the relationship of one's gums to the teeth, the interproximal gap between adjacent teeth and the depth of pockets within the sulcus. For individuals who have had periodontal surgery, plural strands of plural-ply acrylic fiber have been found to be an effective hygienic apparatus. Dental implants involve the use of support posts which elevate the implanted teeth above the gum. This provides a space which is inaccessible by normal flossing unless a leader is used.

A fourth known reason involves the beneficial characteristics of acrylic fiber as a flossing tool. The acrylic fiber appears to have the requisite absorbency to actually serve as a carrier in removing unwanted plaque. Thus, whereas the fibers initially served to break up the film placed on the teeth and gums of the flosser, the fibers also absorb the plaque and remove it from the site of potential harm. The floss thus buffs the plaque off.

A fifth reason involves the disturbance of existing sites of necrosis and festering inflammation. When the floss is used regularly, objectionable odors associated with halitosis abate as a function of time.

Viewed in its essence, the instant invention is directed to dental floss formed from acrylic fiber integrally coupled to a specially formed leader. The floss may be formed from braiding a plurality of acrylic fiber strands, and in one form of the invention, sets of braided strands are disposed in stacked registry and used simultanously to occupy as much of a gap as exists between adjacent teeth, underlying support tissue and supporting implant posts.

The leader itself works most efficiently when it is of relatively small dimension (compared to the floss cross-section when unstressed) and is somewhat textured. It does not exhibit the same characteristics as the floss (which is intended to contact and remove the plaque) but rather is formed from different material, such as plactic. Consequently, the leader is characterized in its relatively small cross-sectional diameter when compared with the floss and has a substantially lower coefficient of friction than the floss. Thus, the leader can pass between the implant posts, gum and bridgework. The floss itself is then pulled between spaces of the dental appliance.

Striking a balance between forming a leader which does not harm the user's teeth, gums or bridgework and is yet easily graspable is one hallmark of the instant invention. Saliva on plastic renders most leaders hopelessly slippery.

Another hallmark of the instant invention involves the minimal failure rate of the leader and floss at the point of greatest stress—at the trailing end of the leader where the floss contacts the leader.

The essential feature is to attach an extremely small leader in such a way that the floss can be used in relatively tight clearances with minimal dexterity requirements imposed upon the user. Another hallmark of the instant invention is it's ability to be used within the minimal clearances indigenous with the flossing operation and by individuals having relatively modest dexterity skills to increase the likelihood that the user will not be dissuaded from practicing good oral hygiene techniques. It should be noted that any program of oral prophylaxis is predicated on habitual hygienic practices. One characteristic of the instant invention is that it removes many frustrations that attend prior art flossing structure and techniques such as threading the leader and leader failure. Increasing the likelihood that the device will be used on a regular basis with a minimal amount of disruption reinforces pre-existing good dental habits and encourages good new habits.

OBJECTS OF THE INVENTION

Accordingly, it is a primary object of the present invention to provide a new and useful dental flossing implement.

A further object of the present invention is to provide a device as characterized above which is relatively inexpensive to manufacture, benefits from mass production techniques, and is durable and safe to use.

A further object of the present invention is to provide a device as characterized above which efficiently removes plaque from areas not as accessible by known prior art instrumentalities.

A further object of the present invention is to provide a device as characterized above in which the floss has a co-efficient of friction such that the flosser has readily discernable feedback which correlates with the quantum of pressure for efficient use of the floss. The leader is readily graspable yet does not adversely affect one's teeth, gums and dental appliances.

A further object of the present invention is to provide a device as characterized above which can be used as a post-surgical prophylactic and with implant anchored or supported dentures or bridges, as well as standard fixed bridges.

A further object of the present invention is to provide a device as characterized above which includes a plurality of fibrous free ends which can extend into the trough-like recess that exists between supporting soft tissue and the teeth to not only remove plaque but also stimulate the gingiva.

A further object of the present invention is to provide a device for flossing dental appliances such as bridges, implants and the like which includes a leader having a free end and a tethered end, the tethered end including a door and acrylic fiber floss connected to said tethered end via the door such that, during fabrication of the device, the floss is looped about a hinge of the door and the door is shut.

A further object of the present invention is to provide a device as characterized above which includes integrally formed dental floss and leader for use with bridges, implants or the like, the leader have a free end for threading into interproximal dental spaces and a tethered end which supports said floss, the tethered end including the floss precaptured thereto.

Viewed from one vantage point, it is an object of the present invention to provide an integrally formed dental floss and leader for use with bridges, implants or other structures such as teeth and prosthodontic devices. The leader has a free end for threading into interproximal dental spaces and a tethered end which supports the floss. The tethered end includes the floss tethered thereto and a door extending from the tethered end and connected to the tethered end through a hinge. The tethered end also includes a tensile strength enhancement so that the door is pivotable about the hinge and connectable to the tethered end with the floss securely captured between the door and the tethered end.

Viewed from a second vantage point, it is an object of the present invention to provide a device for flossing in which a leader has a free end and a tethered end. The tethered end includes a door attached thereto through a hinge. The tethered end includes a depression which defines a support channel having a shape which conforms to a shape of the door. The support channel is oriented to the hinge in a manner which causes the door to reside within the support channel when the door is pivoted about the hinge. Acrylic fiber floss, having a substantially uniform cross-sectional area along its length and having a plurality of outwardly extending fibrous free ends which contact and remove plaque from the dental environment, is connected to the tethered end via the door such that, during fabrication of the device, the floss is looped about the hinge of the door and the door is shut into the support channel.

Viewed from a third vantage point it is an object of the present invention to provide a method for attaching floss to a leader for use between interproximal spaces of a user's mouth. The steps include forming a tethered end of the leader with a door connected thereto through a hinge. The tethered end has a support channel oriented on a side of the hinge opposite the door; next orienting the floss adjacent the hinge; pivoting the door about the hinge; and securing the door directly to the tethered end fixes the the floss to the leader.

These and other objects will be made manifest when considering the following detailed specification when taken in conjunction with the appended drawing figures.

BRIEF DESCRIPTION OF THE DRAWINGS

FIG. 1 is a plan view of the threaded leader of this application.

FIG. 2 is a side view of that which is shown in FIG. 1 with the door closed but without floss captured thereto.

FIG. 3 is a side view of that which is shown in FIG. 1 with the door open.

FIG. 4 is a plan view of the leader with floss attached thereto.

FIG. 5 is a sectional view taken along line V—V of FIG. 1.

DESCRIPTION OF PREFERRED EMBODIMENTS

Figure 6:
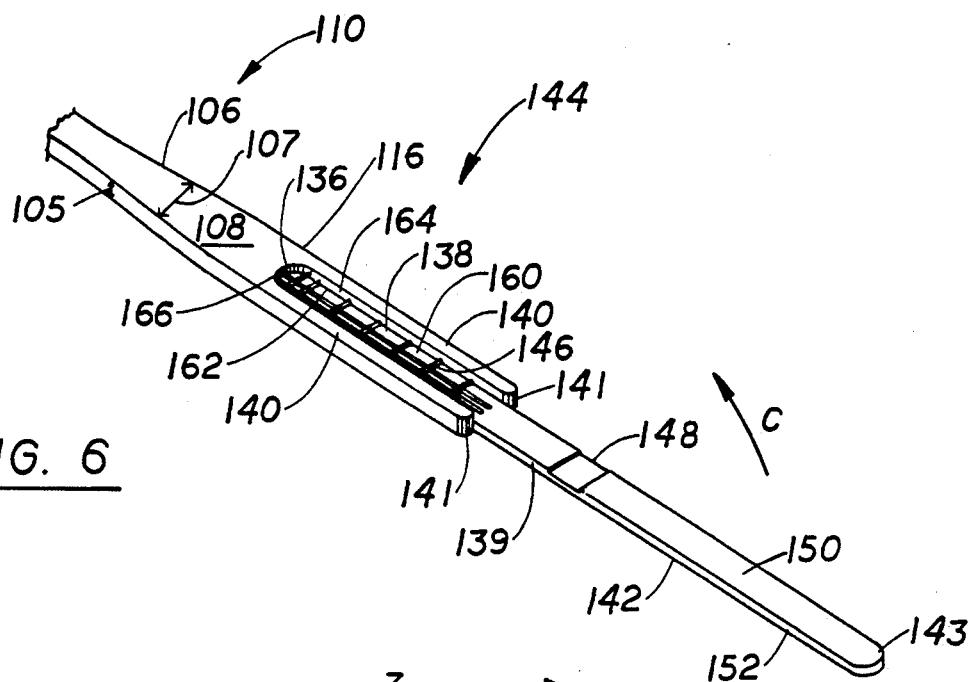
FIG. 6 is a perspective view of that which is shown in FIG. 1 showing details of a portion of the leader before attachment to floss.

Considering the drawings wherein like reference numerals represent like parts throughout, reference numeral 110 is directed to a leader which is attachable to dental floss 50 (FIG. 4) and which has a shape which allows the leader 10 to be easily threaded around bridges, implants or other structures such as teeth and prosthodontic devices.

In its essence, the leader 110 exhibits a narrow curved appearance extending from a free end 102 (FIG. 1) at one end along an arcuate central body 104 to a tapering linear portion 106. The tapering linear portion 106 transitions into a linear portion 116 which supports a leader-floss juncture 144 and defines a tethered end of the leader 110. A plurality of tactile enhancement means 120 are positioned along the arcuate central body 104 of the leader 110.

The tapering linear portion 106 connects the leader-floss juncture 144 to the arcuate central portion 104. The leader-floss juncture 144 includes a depression forming a support channel 138 which has a tongue 139 with a hinge 148 connected thereto which is also connected to a door 142. The door 142 has a contour which conforms to a contour of the support channel 138. The support channel 138 is bounded on either side by shoulders 140. The structure is designed to capture the floss 50 about the hinge 148 with the door 142 nesting flush in channel 138.

Figure 7:
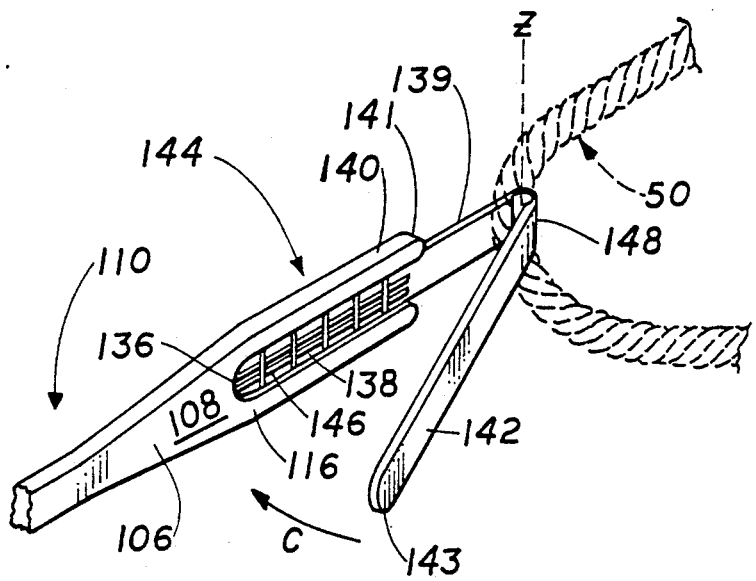
FIG. 7 is a perspective view of that which is shown in FIG. 1 with the floss in the process of being captured by the leader.
Figure 8:
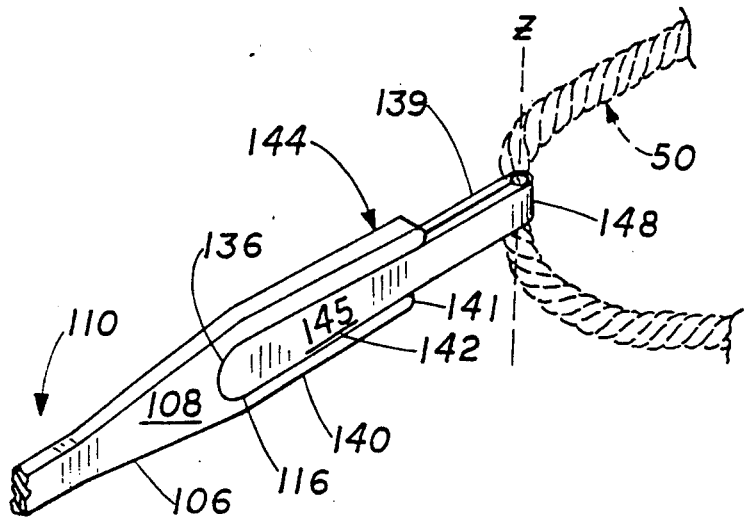
FIG. 8 is a perspective view of that which is shown in FIG. 1 after the floss has been captured by the leader.

More specifically, and referring in detail to FIGS. 6 through 8, the leader-floss juncture 144 includes the following surrounding details. The tapering linear portion 106 has a cross-section of lesser area adjacent to the arcuate central portion 104 (FIG. 1) than its cross-sectional area adjacent the linear portion 116. A first dimension 105, defining a thickness of the tapering linear portion 106 and linear portion 116, remains constant, however. Thus, a second dimension 107, defining a width of the tapering linear portion 106 and the linear portion 116, changes along the tapering linear portion's length. The linear portion 116 has a similar cross-section to that of the tapering linear portion 106 at their interface. The second dimension 107 remains constant along a length of the linear portion 116. Throughout the linear portion's length, the linear portion 116 has essentially a constant rectangular cross-section.

The tapering geometry of the tapering linear portion 106 provides a smooth transition between the arcuate central body 104 (FIG. 1) and the support channel 138. Thus, no areas of high stress concentration are incurred, i.e. areas where the polymer chains defining the plastic material have a weakened portion which are sometimes prone to failure by flexing and can occur during fabrication. Also, having a greater cross-section, the tapering linear portion 106 is more able to withstand bending loads which tend to focus on the leader-floss juncture 144 when flexing the leader.

The width of the linear portion 116 is preferably sized to slightly exceed a width of the tongue 139 plus a double width of the floss 50. In this way, the linear portion 116 is prevented from entering any interproximal space too small to allow the tongue 139 and floss 50 adjacent thereto to pass. If the space is too small, the leader 110 will be blocked at the tapering linear portion 106 and will be easily removed by reversing the direction of the leader 110. The linear portion 116 and tapering linear portion 106 thus act as a floss 50 clearance detection means somewhat analogous to the whiskers of a cat. If the space is too small, the tip 102 and arcuate central body 104 can still be used in a manner similar to that of a toothpick.

The support channel 138 is oriented on a top surface 108 of the linear portion 116. The channel 138 is essentially a box-like depression centered on the top surface 108. The channel 138 has a floor 160 surrounded by an edge 162 which abuts with two parallel linear walls 164 and an arcuate wall 166 joining the two linear walls. The walls 164, 166 are preferably perpendicular to the floor 160. The support channel 138 has a width slightly less than the second dimension 107 of the linear portion 116. Two shoulders 140 are defined by the edges 162 and linear walls 164 of the support channel 138. Each shoulder 140 ends at a curved tip 141 on an end of each shoulder 140 opposite the arcuate central body 104 (FIG. 1). The shoulders 140 enhance the tensile strength of the juncture 144 providing reinforcement means for the tethered end of the leader 110.

Preferably, the support channel 138 has a depth approximately one-half of the first dimension (i.e. thickness) 105 of the tapering linear portion 106. The floor 160 of the support channel 138 is curved at an end opposite the door 142. This curve defines a radiused edge 136 of the channel 138. The arcuate wall 166 extends up from the floor 160 at the radiused edge 136. The floor 160 of the support channel 138 includes sealing beads 146 formed of material which is susceptible to devolution under circumstances such as being exposed to an ultrasonic welding device (not shown) to secure the door shut. The beads 146 are preferably oriented in a plurality of rows some of which are parallel to a long axis of the linear portion 116 and others of which are orthogonal to the linear portion 116.

The floor 160 of the support channel 138 opposite the radiused edge 136 extends beyond the tip 141 of each shoulder 140, thus defining a tongue 139. An end of the tongue 139 distant from the channel 138 has a hinge 148 attached thereto. The hinge 148 in turn has the door 142 attached thereto. The door 142 and tongue 139 preferably have a similar width and a similar thickness. This thickness is preferably somewhat less than half the thickness of the linear portion 116, as defined by the dimension 105. Preferably this thickness difference is similar to a compressed diameter of the floss 50. Thus, the floss 50 can rest between the tongue 139 and the door 142 with the combined door 142, tongue 139, floss 50 combination only slightly thicker than the linear portion 116.

The hinge 148 is preferably formed by providing an area of lesser thickness between the tongue 139 and the door 142. This area of lesser thickness is more susceptible to tolerating bending loads without fracture. The door 142 has a radiused tip 143 on a end thereof opposite the hinge 148. The tip 143 is complemental to the arcuate wall 166 of the support channel 138. A length of the door 142 from the hinge 148 to the radiused tip 143 is substantially similar to a combined length of the tongue 139 and the support channel 138. Thus, when the door 142 is pivoted about the hinge 148, about an axis of rotation Z and along arrow C, the door 142 is positioned within support channel 138 with the radiused tip 143 adjacent the radiused edge 136.

The door 142 preferably has a width similar to a width of the support channel 138. Thus, when the door 142 resides within the support channel 138, sides 152 of the door 142 are adjacent the linear walls 164 of the channel 138 and shoulders 140. The shoulders 140 and radiused edge 136 act like a door jamb, surrounding and supporting the door 142. The door 142 preferably has a thickness similar to a depth of the support channel 138. This allows a bottom surface 145 of the door 142 to be located flush with the top surface 108 of the linear portion 116 when the door top surface 150 is adjacent the floor 160.

Preferably, the tip 141 of each shoulder 140 is radiused slightly. This prevents the floss 50 from being torn by wearing against an otherwise sharp surface of the shoulder 140. The shoulders 140 provide added rigidity to the leader-floss juncture 144. The shoulders 140 also provide support for the door 142, keeping the door 142 aligned within the support channel 138. Thus, when the leader 110 is in use, the juncture 144 is able to maintain a rigid connection to the floss 50 without either the tapering linear portion 106 or the linear portion 116 bending in an inelastic manner.

A width of the linear portion 116, defined by dimension 107, is preferably slightly greater than a width of tongue 139 plus a double width of the floss 50. When utilizing the leader 110 in an interproximal space the clearance within that space necessarily must allow for the tongue 139 width plus twice the floss 50 width (because the floss 50 extends initially away from the tongue 139 in two directions along axis Z). This combined tongue 139 width and floss 50 width defines a clearance width of the floss 50, tongue 139 combination. By restricting the linear portion 116 to this width, the linear portion 116 provides maximum juncture 144 support while not increasing a functional width of the leader 110.

The juncture 144 avoids high stress concentrations in at least two ways, inter alia. First, the channel 138 is strengthened by providing the shoulders 140 along sides thereof. The shoulders 140 maintain a thickness of the linear portion 116 adjacent the door 142 when closed, providing additional bending resistance. Second, the tongue 139 and door 142 are both formed from a continuous linear segment of material including numerous uninterrupted polymer chains within its microstructure. This prevents weaknesses at locations such as near the tips 141 of the shoulders 140. Providing the channel 138 with the radiused edge 136 also assists in relieving an area of possible localized stress.

A plurality of tactile enhancement means 120 are preferably provided periodically along a single side of the arcuate central body 104, as shown in detail in FIG. 5. The tactile enhancement means 120 are preferably located on the top surface 108 (FIG. 1) and are comprised of a series of individual promenances 122. Each promenance 122 is formed from a raised portion of the arcuate central body 104. The tactile enhancement means 120 allows a user to more successfully grasp the leader 110 during use. Alternatively, the tactile enhancement means 120 can be placed on both sides of the arcuate central body 104.

In use and operation, the leader 110 is coupled to the floss 50 in the following manner. Initially, the floss 50 is preferably located over the tongue 139. The door 142 is then pivoted (along arrow C) about the hinge 148 until the door 142 is located within the support channel 138. The door 142 pivots about axis Z approximately 180°. The floss 50 then becomes captured between the door 142 and the tongue 139 with the floss 50 tangential to axis Z at a point near the hinge 148. An ultrasonic welding device is preferably then utilized to devolve the beads 146 located within the support channel 138. The beads 146 thus bind the door 142 within the support channel 138. Alternatively, other adhesives may be used in place of the beads 146 and the ultrasonic welding device (not shown). The floss 50 is then captured to the leader 110 and is ready for use within a person's mouth.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. An integrally formed dental floss and leader for use with bridges, implants or other structures such as teeth and prosthodontic devices, comprising in combination:
   a leader having a free end for threading into interproximal dental spaces and a tethered end which supports said floss,
   said tethered end including said floss tethered thereto,
   said tethered end including a door means extending from said tethered end and connected to said tethered end through a hinge means,
   said tethered end including a reinforcing means to support and receive said door, said reinforcing means including said tethered end having a plurality of shoulders extending therealong and a support channel extending therealong, said shoulders having a thickness not less than a thickness of said door means plus a thickness of said support channel, such that when said door means is adjacent said support channel, said door means does not extend above said shoulders, and
   wherein said door means is pivotable about said hinge means and connectable to said tethered end with said floss captured between said door means and said tethered end.

2. The device of claim 1 wherein said reinforcement means of said tethered end includes said tethered end configured to have a greater cross-sectional area than said door.

3. The device of claim 1 wherein said reinforcing means of said tethered end is said tethered end having a constant thickness along edges thereof, said tethered end having a thickness less than a thickness along said edges at a location between edges of said tethered end defining said support channel, said support channel having a contour which conforms to a contour of said door, and wherein when said door is pivoted about said hinge means said door rests within said support channel, whereby cross-sectional dimensions of said tethered end remain unchanged by receipt of said door thereagainst.

4. The device of claim 1 wherein a tongue extends away from said tethered end and connects said hinge to said tethered end at a location spaced away from said support channel, said tongue having a thickness similar to a thickness of said door, said tongue having a length not less than a thickness of said floss;

whereby said floss is held between said tongue and said door.

5. The device of claim 1 wherein said tethered end includes clearance detection means, whereby interproximal dental spaces too small to receive floss therein are detected before passage of said tethered end through the space.

6. The device of claim 1 wherein said tethered end and said door are shaped such that when said door is pivoted about said hinge means and attached to said tethered end said door is received within said tethered end, such that cross-sectional dimensions of said tethered end combined with said door are no greater than cross-sectional dimensions of said tethered end alone, whereby said tethered end maintains a low profile after said door is attached to said tethered end preserving the ability of said leader to be threaded into interproximal dental spaces.

7. An integrally formed dental floss and leader for use with bridges, implants or other structures such as teeth and prosthodontic devices, comprising in combination:

a leader having a free end for threading into interproximal dental spaces and a tethered end which supports said floss, said tethered end including said floss tethered thereto, said tethered end including a door means extending from said tethered end and connected to said tethered end through a hinge means, said tethered end including a reinforcing means to support and receive said door, wherein said door means is pivotable about said hinge means and connectable to said tethered end with said floss captured between said door means and said tethered end, wherein said reinforcement means of said tethered end includes said tethered end configured to have a greater cross-sectional area than said door, and wherein said reinforcing means of said tethered end is said tethered end having a constant thickness along edges thereof, said tethered end having a thickness less than a thickness along said edges at a location between edges of said tethered end defining said support channel, said support channel having a contour which conforms to a contour of said door, and wherein when said door is pivoted about said hinge means said door rests within said support channel, whereby cross-sectional dimensions of said tethered end remain unchanged by receipt of said door thereagainst.

8. The device of claim 7 wherein said support channel includes an attachment means therein, said attachment means binding said door to said support channel.

9. The device of claim 8 wherein said edges of said tethered end having said constant thickness define shoulders adjacent to the sides of said support channel, said shoulders having a thickness not less than a combined thickness of said door and said support channel, whereby said tethered end maintains rigidity along said tethered end's length and whereby said door is prevented from pivoting away from said support channel within a plane including said shoulders.

10. The device of claim 9 wherein a tongue extends away from said tethered end and connects said hinge to said tethered end at a location spaced away from said support channel, said tongue having a thickness similar to a thickness of said door, said tongue having a length not less than a thickness of said floss;

whereby said floss is held between said tongue and said door.

11. The device of claim 10 wherein said tethered end includes clearance detection means, whereby interproximal dental spaces too small to receive floss therein are detected before passage of said tethered end through the space.

12. The device of claim 11 wherein said floss clearance detection means includes said tethered end having a maximum width not less than a clearance width of said floss captured between said tongue and said door, whereby a combined width of said tongue and said floss adjacent thereto is always passable through interproximal dental spaces if said tethered end is passable therethrough, thereby preventing entrapment of said floss and said leader within the interproximal space.

13. The device of claim 12 wherein said tethered end and said door are shaped such that when said door is pivoted about said hinge means and attached to said tethered end said door is received within said tethered end, such that cross-sectional dimensions of said tethered end combined with said door are no greater than cross-sectional dimensions of said tethered end alone, whereby said tethered end maintains a low profile after said door is attached to said tethered end preserving the ability of said leader to be threaded into interproximal dental spaces.

14. The device of claim 13 wherein said support channel has a radiused edge at an end of said support channel opposite said tongue and said door has a radiused tip, said radiused edge and said radiused tip having complemental contours;

whereby said radiused tip can reside adjacent said radiused edge when said door is within said support channel.

15. The device of claim 14 wherein said door has a length similar to a combined length of said support channel and said tongue;

whereby when said door is pivoted about said hinge, said radiused tip is located adjacent said radiused edge.

16. The device of claim 15 wherein said reinforcement means of said tethered end includes said tethered end configured to have a greater cross-sectional area than said leader between said free end and said tethered end, an end of said tethered end nearest said free end including a tapering portion with diverging surfaces, whereby a smooth transition to said tethered end is provided.

17. A device for flossing dental appliances such as bridges, implants and the like, comprising in combination:

a leader having a free end and a tethered end, said tethered end including a door attached thereto through a hinge, said tethered end including a depression defining a support channel, said support channel having a shape which conforms to a shape of said door, said support channel oriented to said hinge in a manner which causes said door to reside within said support channel when said door is pivoted about said hinge, and acrylic fiber floss having a substantially uniform cross-sectional area along its length and having a plurality of outwardly extending fibrous free ends which contact and remove plaque from the dental environment, said floss connected to said tethered end via said door such that, during fabrication of said device, said floss is looped about said hinge of said door and said door is shut into said support channel.

18. The device of claim 17 wherein a reinforcing means is provided at said tethered end;
whereby said tethered end is strengthened to avoid separation between said leader and said acrylic fiber floss, said reinforcing means including two shoulders, one on each side of said support channel.

19. The device of claim 18 wherein said tethered end connects to said free end through an arcuate central portion adjacent said free end and a tapering linear portion adjacent said tethered end, said tapering linear portion having diverging surfaces providing a smooth geometric transition between said arcuate central portion and said tethered end;
whereby areas of stress concentration are avoided.

20. The device of claim 19 wherein said tethered end maitains a substantially constant rectangular cross-section along its length and wherein one dimension of said tapering linear portion remains constant along its length with a second dimension increasing toward said tethered end to an amount not less than a combined width of said leader and two strands of said floss, whereby said tethered end defines a point of maximum width, thereby preventing said tethered end from passing through any interproximal space to small to allow said leader and said floss to pass therethrough.

21. The device of claim 17 wherein said tethered end connects to said free end through an arcuate central portion adjacent said free end and a tapering linear portion adjacent said tethered end, said tapering linear portion having diverging surfaces providing a smooth geometric transition between said arcuate central portion and said tethered end;
whereby areas of stress concentration are avoided.

22. The device of claim 17 wherein said tethered end maintains a substantially constant rectangular cross-section along its length and wherein one dimension of said tapering linear portion remains constant along its length with a second dimension increasing toward said tethered end to an amount not less than a combined width of said leader and two strands of said floss, whereby said tethered end defines a point of maximum width, thereby preventing said tethered end from passing through any interproximal space to small to allow said leader and said floss to pass therethrough.

23. A method for attaching floss to a leader for use between interproximal spaces of a user's mouth, the steps including:
forming a tethered end of the leader with a door connected thereto through a hinge, the tethered end having a support channel embedded within the tethered end on a side of the hinge opposite the door;
orienting the floss adjacent the hinge;
pivoting the door about the hinge; and
securing the door directly within the support channel of the tethered end.

24. The method of claim 23 wherein said securing step includes the further step of configuring the door to be complemental in form to the support channel; whereby the door fits securely into the support channel.

25. The method of claim 24 wherein said securing step includes the further step of interposing an adhesive means between the door and the support channel.

26. The method of claim 25 wherein said securing step includes the further step of providing beads between the door and the support channel, the beads formed of a material capable of devolution to bond the door to the support channel.

27. The method of claim 26 wherein said orienting step includes positioning a portion of the floss tangent to an axis of rotation of the hinge, the tangent portion of the floss located between the door and the support channel on a side of the hinge such that said pivoting step captures the floss to the tethered end.

28. The method of claim 27 including the further step of reinforcing the tethered end by locating shoulders along sides of the support channel, the shoulders having a thickness not greater than a thickness of the door and the support channel combined;
whereby the shoulders do not interfere with passage of the leader through interproximal spaces.

29. The method of claim 23 wherein said securing step includes the further step of interposing an adhesive means between the door and the support channel.

30. The method of claim 23 wherein said securing step includes the further step of providing beads between the door and the support channel, the beads formed of a material capable of devolution to bond the door to the support channel.

31. The method of claim 23 wherein said orienting step includes positioning a portion of the floss tangent to an axis of rotation of the hinge, the tangent portion of the floss located between the door and the support channel on a side of the hinge such that said pivoting step captures the floss to the tethered end.

32. The method of claim 23 including the further step of reinforcing the tethered end by locating shoulders along sides of the support channel, the shoulders having a thickness not greater than a thickness of the door and the support channel combined;
whereby the shoulders do not interfere with passage of the leader through interproximal spaces.

33. An integrally formed dental floss and leader for use with bridges, implants or other structures such as teeth and prosthodontic devices, comprising in combination:
a leader having a free end for threading into interproximal dental spaces and a tethered end which supports said floss,
said tethered end including said floss tethered thereto,
said tethered end including a door means extending from said tethered end and connected to said tethered end through a hinge means,
said tethered end including a reinforcing means to support and receive said door,
wherein said door means is pivotable about said hinge means and connectable to said tethered end with said floss captured between said door means and said tethered end, and
wherein said tethered end has a before door closure thickness not less than an after door closure thickness and a before door closure width not less than an after door closure width, whereby the thickness and width of said tethered end is not increased by closure of said door means.

* * * * *